(12) United States Patent
Du et al.

(10) Patent No.: US 11,486,548 B2
(45) Date of Patent: Nov. 1, 2022

(54) SYSTEM FOR DETECTING CRACK GROWTH OF ASPHALT PAVEMENT BASED ON BINOCULAR IMAGE ANALYSIS

(71) Applicant: Yuchuan Du, Shanghai (CN)

(72) Inventors: Yuchuan Du, Shanghai (CN); Xiaoming Zhang, Shanghai (CN); Shengchuan Jiang, Shanghai (CN); Yue Qiu, Shanghai (CN); Guangzhao Chang, Shanghai (CN); Lijun Sun, Shanghai (CN)

( * ) Notice: Subject to any disclaimer, the term of this patent is extended or adjusted under 35 U.S.C. 154(b) by 250 days.

(21) Appl. No.: 16/474,710

(22) PCT Filed: Dec. 30, 2017

(86) PCT No.: PCT/IB2017/058549
§ 371 (c)(1),
(2) Date: Jun. 28, 2019

(87) PCT Pub. No.: WO2018/122819
PCT Pub. Date: Jul. 5, 2018

(65) Prior Publication Data
US 2019/0339209 A1    Nov. 7, 2019

(30) Foreign Application Priority Data

Dec. 30, 2016    (WO) .................... PCT/IB2016/58109

(51) Int. Cl.
*E01C 23/01*    (2006.01)
*G01N 21/88*    (2006.01)
(Continued)

(52) U.S. Cl.
CPC ................ *F17D 5/02* (2013.01); *E01C 23/01* (2013.01); *G01M 3/002* (2013.01);
(Continued)

(58) Field of Classification Search
None
See application file for complete search history.

(56) References Cited

U.S. PATENT DOCUMENTS 4,899,296 A * 2/1990 Khattak ................. G01N 3/068
                                                                    73/146
6,615,648 B1 * 9/2003 Ferguson ................. G01C 7/04
                                                                    73/146
(Continued)

FOREIGN PATENT DOCUMENTS

CN    101701919    5/2010
CN    102108666 A    6/2011
(Continued)

*Primary Examiner* — Matthew G Marini (57) ABSTRACT

A binocular image analysis-based asphalt road surface damage detection system, comprising five sub-systems for crack development degree detection model establishment, information collection, information analysis, information transmission and information distribution. Specifically, road surface damage information detection is performed by means of a mobile platform, a processing end, a temperature measurement-type infrared thermal imaging instrument, an ordinary image collector, a vibration sensor, image processing technology, edge cloud computing technology, an embedded system, system integration technology and real-time positioning technology.

16 Claims, 6 Drawing Sheets

(51) Int. Cl.
- *F17D 5/02* (2006.01)
- *G01M 3/00* (2006.01)
- *G01M 5/00* (2006.01)
- *G01N 21/95* (2006.01)
- *G01N 33/42* (2006.01)

(52) U.S. Cl.
CPC ........ *G01M 5/0033* (2013.01); *G01M 5/0066* (2013.01); *G01N 21/95* (2013.01); *G01N 33/42* (2013.01); *G01N 2021/8845* (2013.01)

(56) References Cited

U.S. PATENT DOCUMENTS

| | | | |
|---|---|---|---|
| 2011/0221906 A1* | 9/2011 | Xu | G01N 21/95 |
| | | | 348/148 |
| 2016/0350907 A1* | 12/2016 | Simula | G01N 33/42 |
| 2020/0118263 A1* | 4/2020 | Nogami | G06T 7/11 |

FOREIGN PATENT DOCUMENTS

| | | |
|---|---|---|
| CN | 102182137 A | 9/2011 |
| JP | 0981138 | 3/1997 |

* cited by examiner

SYSTEM FOR DETECTING CRACK GROWTH OF ASPHALT PAVEMENT BASED ON BINOCULAR IMAGE ANALYSIS

TECHNICAL FIELD

The invention belongs to the field of intelligent transportation system and information technology and relates to five sub-systems: detection model formulation of crack growth degree, information collection, information analysis, information transmission and information release. Specifically, it includes mobile platform, processing terminal, thermometric infrared thermal camera, general image collector, vibration sensor, image processing, edge cloud computing, embedded system, system integration, real-time positioning technology to carry out crack information detection. Crack information includes number, type, location, and crack growth degree. By introducing infrared thermal image, the gray scale information and temperature information of asphalt pavement crack can be obtained. The gray scale information can realize the target of conventional image-based crack identification, and the temperature information can be used to detect the crack growth degree. The crack detection system on the mobile platform can be realized by using the above technology to achieve fast and accurate detection asphalt pavement crack.

BACKGROUND TECHNOLOGY

With the development of road traffic, the maintenance and management problem of pavement has become increasingly prominent, and the crack detection has become a work focus of the relevant road maintenance department. However, in China the pavement management system is developed mainly by manual detection nowadays with relatively low efficiency and interference of subjective factors. With the rapid development of digital image processing technology in recent years, many researchers at home and abroad have conducted extensive research on image recognition of pavement cracks and got fruitful achievement. However, the existing pavement detection vehicle with multi-dimensional comprehensive and sophisticated technology is expensive and the use cost is high. Moreover, it is difficult to achieve full coverage high-frequency inspection of all levels of roads, resulting in insufficient decision support data for intelligent maintenance. Therefore, the high-frequency inspection equipment covering all levels of roads is urgently needed to collect sufficient crack data for decision support and realize the intelligent management of the entire road network.

(1) N–1 Pavement Inspection Vehicle, Nanjing University of Science and Technology In 2002, Zhao Chunxia and Tang Zhenmin from Nanjing University of Science and Technology successfully developed the N–1 type pavement detection vehicle. The vehicle can collect pavement crack image, smoothness, rutting and other data under 70 km/h driving condition, then process data offline and generate report forms. Vehicle global positioning system and forward-looking color camera are adopted. This vehicle has promoted the development of automatic pavement detection vehicle in China.

(2) CiCS Pavement Inspection Vehicle of Highway Science Research Institute

In 2006, Zhonggong High-Tech Maintenance Technology Co., Ltd, a subsidiary company of Beijing Highway Science Research Institute, developed the pavement detection vehicle of its own intellectual property rights, CiCs. The system uses linear array camera to collect pavement images combined with structural illumination. The detection width can reach 3.6 meters transversely. The maximum detection accuracy is 1 mm and the maximum speed is 100 km/h. CiAS (Cracking Image Analysis System), a pavement disease treatment software developed by the company, can automatically process key pavement indicators including cracks, rutting and smoothness.

(3) ZOYON-RTM Pavement Detection Vehicle

In 2007, Wuhan ZOYON Science and Technology Co., Ltd and Hubei Heli Vehicle Manufacturing Co., Ltd jointly developed the ZOYON-RTM intelligent pavement vehicle. The car uses a high-precision line-array camera to capture the pavement image and adopts laser lighting technology. Uninterrupted acquisition of pavement images is achieved under the control of the encoder's synchronous trigger signal. The system has a crack resolution of up to 1 mm, a maximum detection width of 4 m and a top speed of 120 km/h.

Prior Art 1

Patent document CN200910222882.5, discloses an image-based pavement crack detection system. The system comprising:

the control module, generating a trigger signal according to the received GPS positioning information and outputting a trigger signal to the image acquisition module; the image acquisition module, according to the received trigger signal acquiring image of pavement and road sign and outputting the image to the data processing module;

the data processing module, splicing the first digital image to obtain a continuous digital image of pavement, identifying the first digital image including the crack, the GPS positioning information, and the second digital image, determining the position information of the crack according to the GPS positioning information and the second digital image and outputting. The invention also provides a theory of an image-based pavement crack detection method. With the disclosed system and method, the accuracy and detection efficiency can be increased.

Prior Art 2

Patent document CN201310252824.3 discloses a pavement crack detection system, which includes an information acquisition system, a data storage display system, a power management system, a data processing system, and a GPS positioning system. The information of the pavement disease is recorded by the information acquisition system, the GPS and mileage station are used to locate the disease. The digital image processing technology of the data storage display system is used to identify the disease, so as to obtain objective and stable detection results. The invention can quickly and accurately locate and measure the crack. The invention aiming at the pavement crack detection, realizes the real-time monitoring of related information, data storage and playback, real-time correlation between GPS information and mileage station number, and measurement of crack state information, and designs an on-board detection system to meet the application of actual pavement crack detection.

Prior Art 3

Patent document CN201410269998.5 discloses a pavement crack detecting device based on depth and gray image, comprising: a carrier platform (1) a camera on the carrier platform (6), a line laser (7), a computing device (8). The carrier platform (1) is used to move along the road direction during the crack detection process, and the line laser (7) is used to illuminate the vertical road surface while the carrier platform (1) moves, and the camera (6) is used to move the laser beam reflected by the linear laser through the pavement at an oblique angle and not far away while the carrier platform (1) is moving and shot each road section to generate road data from laser lines of a plurality of road sections. The computing device (8) is configured to generate depth data and gray scale data of road section, and splicing the data for crack identification.

Term Specification

Crack growth degree: Crack growth degree mentioned in the invention characterizes the extent of damage to the pavement caused by cracks in the asphalt pavement and the severity of recent disease. It covers the traditional crack severity classification, related to the width, the depth and the humidity of the crack and other factors that may increase the severity of crack. It characterizes the level of development of cracks from the beginning to the present.

Classification function: The temperature difference data is linearly classified according to the crack growth by Support Vector Machine. The crack growth is divided into three levels of 1, 2, and 3, and 3 is the most serious. Then there will be one dividing line between 1, 2 and 2, 3, the expression of which is the classification function.

Crack area: An area of asphalt pavement that includes not only the crack area itself, but also a certain range around it, meeting the requirements of image processing and crack identification.

Reference temperature difference data: temperature difference data obtained by taking the measured atmospheric temperature into two classification functions.

Measured temperature difference data: temperature difference data of the crack area and the pavement in the crack area obtained by image processing from the acquired infrared image of the crack area.

Crack growth level: A certain number of 1, 2 or 3 whose size reflects the degree of crack growth. The larger the number is, the more serious the crack growth will be.

Processing terminal: Responsible for collecting the raw data, storing and real-time processing, and finally transmitting the processed data wirelessly to the remote server.

Support Vector Machine: Support Vector Machine (SVM) is a machine learning method based on statistical learning theory, which is developed in the mid-1990s. It seeks to minimize the structural risk and improve the generalization of learning machine to achieve the minimum experience risk and confidence range, which achieves good statistical regularity even the case size is very small. In machine learning, Support Vector Machine (SVMs, which also support vector networks) is a supervised learning model related to learning algorithms that can analyze data, identify patterns, and use for classification and regression analysis. Given a set of training samples, each marked as belonging to two categories, a SVM training algorithm builds a model, assigning new instances to one class or other classes, making it a non-probabilistic binary linear classification. Generally speaking, it is a two-class classification model. The basic model is defined as the linear classifier with the largest interval in the feature space. That is, the learning strategy of the Support Vector Machine is to maximize the interval and finally transform into a convex quadratic planning problem.

Algorithm for pavement disease identification model: According to the gray pattern of asphalt pavement, the presence or absence of cracks and the type of maturity algorithm can be obtained. Both the normal image and the infrared image can obtain the gray map.

SUMMARY

The invention provides a pavement disease detection system based on infrared binocular image analysis and power spectral density. The system comprises five subsystems: detection model formulation of crack growth degree, information collection, information analysis, information transmission and information release.

Ordinary images only obtain the gray scale information of asphalt pavement and cracks. The reason why ordinary images are difficult to identify the cracks in asphalt pavement is that the granularity of asphalt pavement affects the identification of crack.

Conventionally, crack growth is identified by the width of the crack, which is determined by identifying the number of pixels in the short side of the crack area, combined with the height at which the camera is located. However, this width-related method is unreliable. Because the crack width of a few millimeters may have only a few pixels in the image, and is subjected to image processing such as noise reduction. The result is more unstable, so it is difficult to identify the crack growth only by the gray scale information from the ordinary image.

Figure 2:
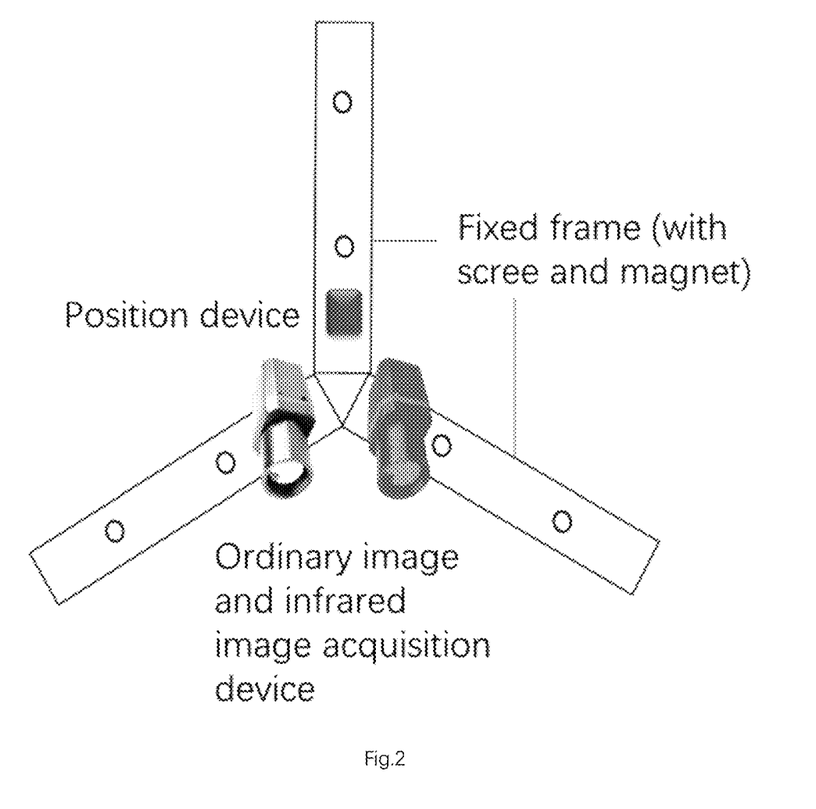
FIG. 2 is the schematic diagram of the fixing collection device.

The infrared thermal image obtained by infrared thermal camera can not only obtain the gray scale information but also obtain temperature information. As shown in FIG. 2, which is the gray scale information and temperature information of the pavement and crack.

Due to the hysteresis and accumulation of pavement temperature, the temperature below the pavement and the pavement is different. Therefore, heat exchange happen between the material below the pavement and the pavement as well as air through the crack. The temperature between the pavement and the crack is also different. The greater the crack width and depth of the asphalt pavement is, the more intense the heat exchange is, accompanied with larger temperature difference. The greater the depth of the crack, the more likely the future water damage will occur. The crack growth index reflects the crack growth. Therefore, the more severe the crack is, the greater the temperature difference between the pavement and the crack is. We can use the thermal camera to detect the temperature difference and then detect the crack growth.

The acceleration change during the running of the vehicle is mainly caused by the change of the road elevation. Therefore, the road elevation change is regarded as the system excitation, the acceleration of the vehicle is regarded as the system response. The conversion formula of the international roughness index (IRI) and the spoke acceleration power spectral density can be derived based on the power spectral density and the linear time-invariant system theory. The calculation accuracy is improved by measuring the acceleration values of different positions in the vehicle. The vehicle speed correction coefficient can correct the influence of the vehicle speed change on the calculation result. At the bridgehead jumping position, based on the acceleration values measured at different positions in the vehicle, combined with the human vibration sensing function and the annoyance rate, the influence of the bridgehead jump on the human comfort is calculated. Considering the impact coefficient and the system response method, the equivalent impact force of the bridgehead is estimated. Adopting the system response method, the detection model of the pavement roughness is indirectly estimated by measuring the Z-axis acceleration variation of the vehicle. The method has the advantages of convenience, low consumption and economic rationality. And it is suitable for measuring a wide range of pavement roughness. In addition, using the mature mathematical methods such as wavelet theory, Kalman filter, linear time-invariant system, and annoying rate in experimental psychology, we can evaluate the phenomenon of bridgehead jumping.

Considering the correlation between Z-axis acceleration and IRI, field measurement through a three-axis gravity acceleration sensor is performed to collect data.

Therefore, in order to quantitatively investigate the influence of speed on the results, we choose different speeds on the same test road to observe the difference of results. After field test, we found that there is a good secondary correlation between speed and power spectral density. The following formula (1):

$$PSD=0.0263v^2+0.6027v \qquad (1)$$

Here, $R^2=0.9991$, proving that the fitness is extremely high. Then the expression is taken into the IRI prediction formula derived above, and the final IRI expression can be obtained.

$$IRI = 0.782\alpha x_{left} + 1.300\alpha x_{right} - 3.442 \qquad (2)$$

$$\alpha = \frac{1}{\sqrt{0.0003865v^2 + 0.0009125v}}$$

The detection method of the pavement crack growth based on infrared thermography is used to construct the detection system. The actual detection system needs the infrared binocular camera to collect the pavement image. The infrared binocular camera includes an ordinary camera and an infrared camera, which simultaneously collects the image of the asphalt pavement and processes it to identify the presence, absence, location, size and growth degree of the crack. The data fusion of the two images can improve the robustness of the detection method.

Modular design is adopted in the detection system and can be combined with other pavement disease detection modules. The crack detection module includes a camera fixing device, a binocular camera, data transmission lines, a vehicle terminal, a GPS receiving device, and an inertial navigation. The camera fixing device can be customized with a metal frame to ensure that the binocular camera can be reliably fixed on the vehicle. The vehicle-mounted pan/tilt can be used to control the angle of binocular camera. The pan/tilt has at least two degrees of freedom. It can rotate in the horizontal and vertical directions respectively, and more degrees of freedom will bring higher operability. The minimum configuration of the infrared camera is 320×240 resolution, replaceable lens, maintenance-free uncooled microbolometer, microscopy and close-up measurement, data transfer speeds up to 60 Hz. The common camera supports real-time output of 1080P HD images. At least two data transmission lines respectively support high-frequency transmission of high-definition ordinary images and infrared images as well as 1080p video transmission at least 100 Hz. The vehicle terminal includes two schemes. One is the front-end processing, where the embedded PC is used for real-time video stream processing, and the data transmission is processed through the 3g\4g network. The embedded PC can be compatible with the data interface of the ordinary image and the infrared image. The processing terminal supports the real-time processing of the video stream. The other one is the back-end processing. The vehicle-mounted terminal serves as the front end of the data acquisition, and is only responsible for data acquisition and storage. The configuration and development requirements are lower, and an interface is required for the third-party device accessed to perform data processing. This module restores the longitudinal image of the pavement through the video image stitching technology, and then cuts it along the length direction to identify the accuracy while ensuring the stability of the asphalt pavement crack detection. This system idea has high requirements for image processing algorithms and relatively few devices. The GPS receiving device and the inertial navigation ensuring the accurate and real-time location of the acquisition device. The accuracy of positioning needs to be within 10 m.

Another crack detection module includes a camera fixing device, a binocular camera, data transmission lines, a vehicle terminal, a GPS receiving device, an inertial navigation, a photoelectric encoder, and a synchronization controller (referring to CN104749187). The photoelectric encoder is mounted on a wheel central axis of the vehicle mobile platform for measuring the speed and moving distance. The GPS receiver is mounted on the vehicle mobile platform for high-precision positioning. The inertia navigation, which is installed on the vehicle-mounted mobile platform, is used for measuring the position and posture data of the vehicle-mounted mobile platform in the case that the GPS receiver in the tunnel does not receive the GPS signal, thereby realizing high precision of the position estimation in the tunnel interior. The synchronization controller, installed on the vehicle mobile platform, is used to synchronize the image acquisition time of the ordinary camera and the infrared camera to ensure a uniform time and space reference. This method accurately measures the vehicle speed through the photoelectric encoder. The synchronous controller automatically controls the binocular image acquisition time according to the vehicle speed and the field of view of the binocular camera to ensure continuity of the images.

The lanes are completely covered and do not overlap each other. After the image is transmitted to the vehicle terminal for the front-end processing or storage function. This system has higher requirements on the device and lower image processing algorithms.

Subsystem 1: Detection Model Formulation of Crack Growth Degree

Figure 1:
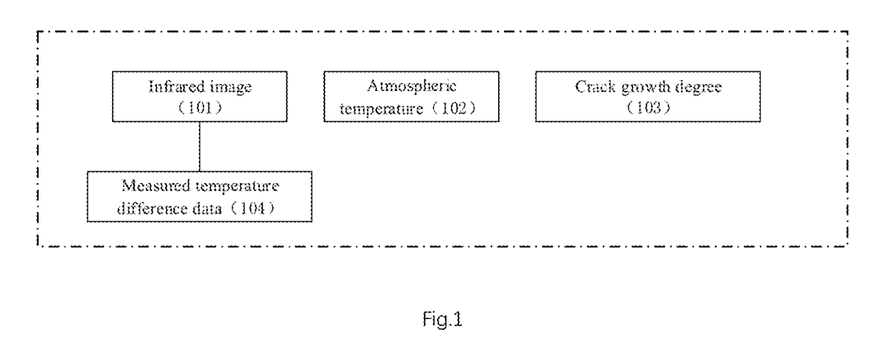
FIG. 1 is the schematic diagram of model formulation of system sampling data, including infrared image (101), atmospheric temperature (102), crack growth degree (103), measured temperature difference data (104)

At least 10 samples for the infrared images of crack area of the asphalt pavement is collected. The atmospheric temperature and the crack growth degree of the samples are recorded. Then the temperature difference data of the sample is obtained after the image processing. Taking the atmospheric temperature as the abscissa, the temperature difference data of the crack area and the pavement area in the corresponding infrared image is plotted on the ordinate as the coordinate point. The sample data required in the model formulation phase is shown in FIG. 1.

Figure 8:
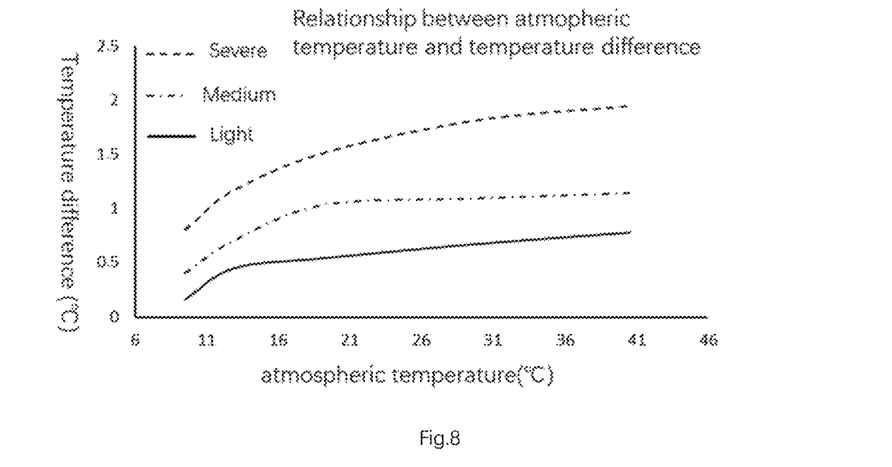
FIG. 8 shows the relationship between atmospheric temperature and temperature difference.
Figure 9:
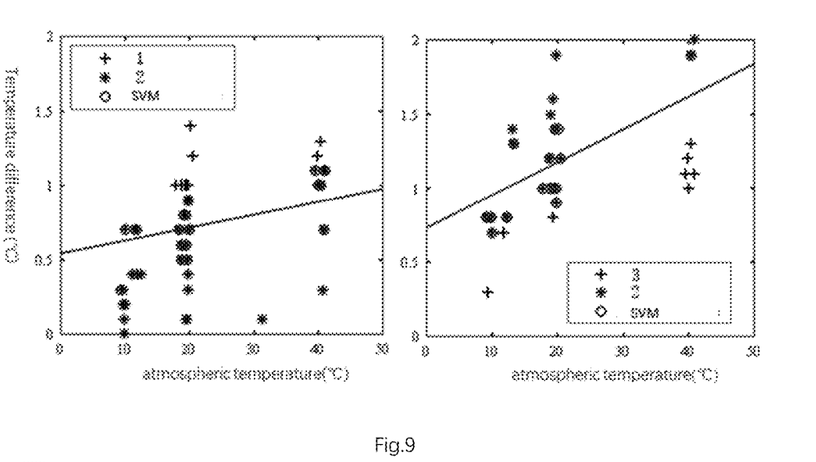
FIG. 9 is a support vector machine linear classification diagram.

Support vector machine is adopted for the data linear classification. Taking the atmospheric temperature as the abscissa, the temperature difference of crack and pavement as the ordinate to draw points, there are three levels of 1, 2, and 3. The greater the number is, the more serious the crack growth is. The classification function graph is shown in FIG. 8 as follows. The classification function is shown in equation (4)(5).

The classification function of level 3 and 2:
$$\Delta T_{23}=a_{23}T+b_{23} \qquad (4)$$

Where T (° C.) is the atmospheric temperature, $\Delta T$ (° C.) is the temperature difference of crack and pavement; $a_{23}$ is the linear classification function coefficient, ranging from 0.02 to 0.03, and $b_{23}$ is the constant term, ranging from 0.60 to 0.85.

The classification function of level 2 and 1:
$$\Delta T_{12}=a_{12}T+b_{12} \qquad (5)$$

Where T (° C.) is the atmospheric temperature, $\Delta T$ (° C.) is the temperature difference of crack and pavement; $a_{12}$ is the linear classification function coefficient, ranging from 0.0075 to 0.0100, and $b_{12}$ is the constant term, ranging from 0.4 to 0.65.

The test results are judged according to the following steps:

First, calculate $\Delta T_{12}$ and $\Delta T_{23}$ according to the atmospheric temperature and compare $\Delta T$ with $\Delta T_{12}$ and $\Delta T_{23}$. If $\Delta T \leq \Delta T_{12}$, crack growth degree is 1; If $\Delta T_{12} \leq \Delta T \leq \Delta T_{23}$, crack growth degree is 2; If $\Delta T \geq \Delta T_{23}$, crack growth degree is 3;

Data acquisition is now performed on other asphalt roads to verify the accuracy of the aforementioned test models. From the above analysis, in the case of completely dry road surface, the temperature difference of crack and pavement is related to the atmospheric temperature and the degree of crack growth. So, the temperature difference of crack and pavement can be detected by the infrared camera.

The classification function is used to detect the degree of crack growth. The test environment is supposed to meets the requirements as described above: during sunny day between 8 am and 4 pm, the road surface is clean and completely dry. Then use the infrared camera to collect data, and record the temperature when each picture is collected. After processing, the temperature difference of crack and pavement is obtained, and the crack growth degree threshold $\Delta T_{12}$, and $\Delta T_{23}$ is calculated according to the temperature.

TABLE 2

Model verification result

| Crack growth level | Actual amount | Theoretical amount | Relative error |
| --- | --- | --- | --- |
| light | 28 | 23 | 17.8% |
| medium | 17 | 15 | 11.8% |
| severe | 12 | 10 | 16.7% |

As shown in Table 2, the relative error is less than 20% and the average error is 15.4%. The results show that the accuracy of the prediction model is great. Most of the current crack detection only pay attention to the quantity. This model gives different weights to cracks of different growth levels, providing more accurate references for maintenance and improving social benefits.

Subsystem 2: Information Collection

The data acquisition layer includes a vehicle positioning device, an active infrared image sensor, a thermometric infrared thermal camera, and a three-axis acceleration sensor.

Vehicle positioning device: The vehicle-mounted mobile measurement system has been applied in many projects such as urban planning, pavement inspection, digital city, etc., and has become an important direction of current surveying and mapping. In order to achieve high-precision vehicle-mounted mobile measurement, higher requirements on the Global Navigation Sat-elite System (GNSS) is put forward. The characteristics of the mobile measurement system determine that the on-board GNSS positioning requires high precision, high frequency and fast dynamic positioning. At present, with the completion of China Bei Dou Navigation Satellite System (BDS), the revival of the Russian GLONASS system and the modernization of the US GPS system, more navigation satellites of great quality will come true. Multi-system observations can greatly increase the number of observation satellites and significantly change the geometric distribution of satellites. The invention adopts the latest BDS or GPS positioning technology to realize accurate real-time refresh of vehicle position information, and the device can continuously transmit position information, including time, latitude and longitude to the processing terminal in a certain frequency range.

Infrared camera is supposed to be protected from direct light source, because the infrared light power control part is based on the photosensitive resistor installed on the infrared light board to control the working power.

Working field should try to avoid all black objects, open spaces, water and other objects that absorb infrared light. The infrared light of CCD camera reflected on the object form an image on the CCD camera lens. If infrared light is absorbed or weaken, the effective illumination of the infrared lamp will be reduced.

The active infrared image sensor device realizes the detection of grayscale image acquisition of the pavement, and the image quality is at least 720p. The active infrared image sensor is supposed to support wired transmission of digital image to the processing terminal.

The thermometric infrared thermal camera: Until the 1960s, thermal imaging technology had been used in non-military applications. Although early thermal imaging systems is cumbersome, slow in data acquisition and poor in resolution, they were used in industrial applications such as inspection of large electricity transmission and distribution systems. In the 1970s, the continued development of military applications led to the first portable system. The system can be used in applications such as building diagnostics and non-destructive testing of materials.

The thermal imaging systems of the 1970s were rugged and very reliable, but their image quality was poor compared to modern thermal imaging cameras. By the early 1980s, thermal imaging technology has been widely used in medical, mainstream, and architecture inspections. Once calibrated, the thermal imaging system can produce a complete image of the radiation so that the radiant temperature at any location in the image can be measured. A radiation image is a thermal image that contains calculated values of temperature measurements at various points within the image.

The safe and reliable thermal imager cooler has been modified and now it hase replaced the long-established compressed or liquefied gas used to cool the thermal imager. In addition, a lower-cost PEV thermal imaging system has been developed and mass produced. Although radiation measurements are not possible, the PEV thermal imaging system is lightweight, easy to carry, and operates without cooling.

In the late 1980s, a new equipment called the Focal Plane Array (FPA) come to the commercial market from military applications. FPA is an image sensing device composed of infrared sensing detectors arrays (usually rectangular) located at the focal plane of the lens.

The parameters of the thermometric infrared thermal camera refer to the following but are not limited to:

Spatial resolution: 0.68 mrad;
Image frequency: 50 Hz (100/200 Hz with window);
FPA/wavelength range: uncooled microcalorimeter/ 7.5~14 um;
Infrared resolution: 640×480 pixels;
Object temperature range: −20° C.~120° C.;
Support USB and ethernet image stream output.

The thermometric infrared thermal camera needs to realize the infrared thermal image acquisition of pavement. So, the temperature information of crack and pavement can be obtained.

Three-axis acceleration sensor: Three-axis acceleration sensor mostly use piezoresistive, piezoelectric, and capacitive operating principles. The resulting acceleration is proportional to changes in resistance, voltage, and capacitance, and is collected by corresponding amplification and filtering circuits, following the same principle as the ordinary acceleration sensor. So, in a certain technology, three single axes can be turned into a three-axis one. Two-axis accelerometers can already meet the requirement of most sensor applications. However, some applications are concentrated in three-axis accelerometers such as digital mining equipment, valuable asset monitoring, collision monitoring, architecture vibrations monitoring, wind turbines, wind turbines and other sensitive large structural vibrations.

The invention adopts an integrated acceleration sensor. The sensor module has an infinite transmission module and a lithium battery, which can realize the vibration signal acquisition of the vehicle rear axle. The frequency can be up to 200 Hz.

In the above equipment, the acceleration sensor is a collection device of the roughness detection module, and the two cameras are acquisition devices for pavement disease detection such as cracks, and the positioning device is an auxiliary device for realizing automatic detection processing. The acquisition equipment and auxiliary equipment of each module can be designed with reference to FIG. 2 below, and can be fixed on various mobile platforms. The vehicle mount includes two camera platforms and three fixed frames, each of which has two to four magnet adsorption devices. Two camera platforms can be fixed by using magnet adsorption devices on the three fixed frames. At the same time with two screw holes, it is necessary to use screws to fix the acquisition system to the vehicle. The fixed frames need to ensure the stability of the camera and the reliability during rapid moving.

Subsystem 3: Information Transmission

The data transmission layer includes two methods: wired transmission and wireless transmission.

The wired transmission includes two channels of video and positioning information. The ordinary image adopts a high-definition video transmission line. The infrared image can be transmitted by using a high-definition video transmission line or a network cable. The transmission of the vibration signal adopts the wireless transmission mode. Referring to the zigbee or WIFI mode, the invention adopts the zigbee transmission mode, and wifi is used as the technical reserve.

Simply\ZigBee is a highly reliable wireless data transmission network similar to CDMA and GSM networks. The ZigBee data transmission module is similar to a mobile network base station. The communication distance is from standard 75 m to several hundred meters, several kilometers, and supports unlimited expansion. ZigBee is a wireless data transmission network platform consisting of up to 65,000 wireless data transmission modules. Throughout the network, each ZigBee network data transmission module can communicate with each other. The distance between each network node can unlimitedly extend from standard 75 m.

Different from the CDMA network or GSM network of mobile communication, the ZigBee network is mainly established for automation control data transmission in industrial field. Therefore, it should simple, practical, reliable in operation and low in price. The mobile communication network is mainly established for voice communication. Each base station is generally more than one million yuan, and each ZigBee "base station" is less than 1,000 yuan. Each ZigBee network node can not only be used as a monitoring object and can also automatically transfer data transmitted from other network nodes. In addition, each ZigBee network node (FFD) can also wirelessly connect with multiple isolated child nodes (RFD) that do not undertake network information relay tasks within the scope of their own signal coverage.

Figure 3:
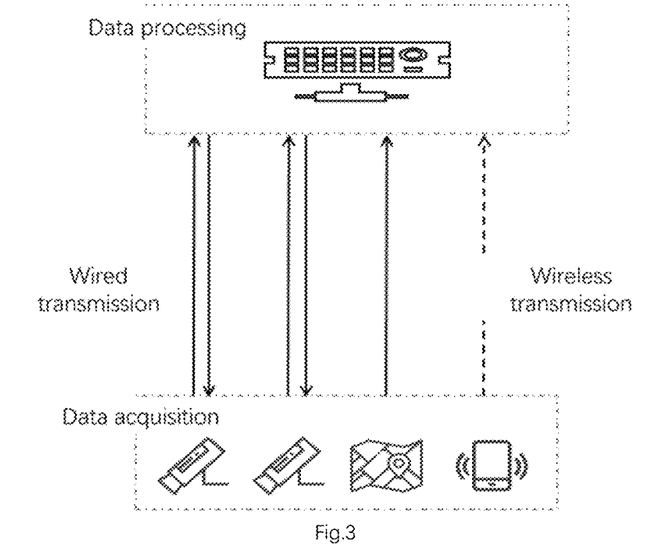
FIG. 3 is the schematic diagram of the acquisition terminal and the processing layer.

Data transmission is designed on the principle of reliability, real time and stability to ensure efficient communication between the data processing layer and the data acquisition layer. At the same time, the command information of the control terminal needs to be sent to the acquisition device. The network transmission is shown in FIG. 3.

The built-in data storage device and processing end, and mainly stores system processing logs, original disease image data, original vibration data, and their corresponding spatial and temporal coordinates for further processing and large data accumulation.

The real-time transmission is only for the disease information after the data processing, and mainly uses the wireless network for transmission, including the 3g/4g network. The narrowband IoT transmission technology is used under the conditions allowed. The data transmission layer is only one-way transmission from the processing terminal to the server center.

Subsystem 4: Information Analysis

The data processing layer includes general image processing, infrared image processing and vibration signal processing. The image frame containing crack obtained by the image processing is matched with the position information to obtain the pavement disease type and position. The roughness along the road and the abnormal jumping information are further obtained by processing the vibration signal matched with the position information.

Ordinary image processing: Firstly, the image needs to be grayed out and noise-reduced. Image denoising is suitable for ordinary images and infrared images. In reality, digital images are often affected by imaging equipment and external environmental noise during digitization and transmission, which is called noisy images or images with noise. The process of reducing noise in digital images is called image denoising. Noise is an important cause of image interference. An image may have a variety of noises in practical applications, which may be generated in transmission or processing such as quantization.

The methods of image denoising are shown as follows, mean filter, adaptive Wiener filter, median filter, morphological noise filter, wavelet denoising, etc.

Edge detection is a common detection process in application, because the features of interest usually have significant changes in the local gray scale of the image, which are quite different from the background image. The edge information of the image where these changes are strong can be decomposed into edge direction and edge amplitude characteristics. Usually, the amplitude of the edge changes relatively gently along the edge direction, while the sharp edge changes in the direction of the vertical edge. According to the characteristic of edge, scholars have proposed a number of differential operators based on first or second order to achieve edge detection. Using the discretized gradient approximation function, the position of the gradient transformation can be obtained. Then connect the extreme points in the image to form the edge of the image.

The invention uses the Canny operator for edge detection to identify crack diseases, which is the core algorithm for crack detection. The detection effect of the Canny operator is the most excellent. Its main feature is that the noise control is very good. The pseudo crack can be removed bringing clean image. The morphological processing has great advantages. The key parameters of the Canny operator are the value of Alpha and two high and low threshold parameters. By non-maximal suppression of the gradient amplitude, the division and connection of the pseudo-crack and the double threshold are reduced, so that the edges are continuously integrated and clearly identifiable.

The latter step in the extraction of the edge information is the threshold segmentation. If the appropriate threshold segmentation is not performed, the edge information will be very messy, and the pseudo-cracks occupy the entire image region, so the step of threshold segmentation is crucial. The basic idea of threshold segmentation is based on the difference in the grayscale values between the target and the background in the original image. The image is divided into two parts: the target (foreground) and the background by setting one or more thresholds. Threshold segmentation is mainly divided into global and local threshold methods. The global threshold method includes bimodal method, Otsu method, minimum error method and one-dimensional maximum entropy method. The present invention adopts one-dimensional maximum entropy method.

After edge detection and threshold segmentation of the image, the resulting image will have some extra false edges. The next step is to remove the invalid information, remove the burrs at the edge of the crack and join the edges of the broken crack. The invention employs a mathematical morphology approach to solve these problems. Mathematical morphology is a discipline based on set theory. It is a tool for approximate mathematical analysis of images based on the form of images. The core idea is to measure and process the original image with a structured element with a certain shape. Mathematical morphology can simplify image data and can be applied to areas such as image segmentation, noise suppression, and image restoration. The basic arithmetic operations of mathematical morphology are four: Erosion, Dilation, Opening, and Closing. The combination of the first two operations can form the latter two operations. In the process, the structural element is equivalent to a "filtering window", using this structured element, intersecting it with the image to be processed, and waiting for the set operation. The Erosion can effectively remove the orphans in the segmented image and refine the cracks. In order to approximate the original crack size, Dilation is performed on crack image.

After the aforementioned steps, the characteristics of the crack have been separated from the background image, however, these divided regions usually contain non-crack noise and other interference factors such as oil stains and debris. Therefore, in order to correctly extract the crack, the determination of the crack is a crucial step. The invention utilizes a selection method based on the fusion characteristics of crack, and can achieve a correct rate of more than 90%.

(1) The ratio of the major axis to the minor axis of the minimum external ellipse is defined as the following equation (3):

$$Anisometry = Ra/Rb \qquad (3)$$

The crack usually presents a relatively narrow area in the small image. Each crack Region is circumscribed by an ellipse. The Anisometry parameter of each Region is obtained, and the maximum Anisometry is recorded as the basis for determination.

(2) The Crack Area

Calculate the pixel area of each crack area, save it to the Area array, and extract the Area data of the Region with the largest area. Since the crack usually occupies a larger part of the block area, the area of the remaining pseudo crack is usually small, so that the area of the crack area can also be used as a basis for judging whether it is a crack.

The invention first introduces the idea of block image detection of pavement image, and then performs edge detection on the crack image of the pavement. In the invention, we use an improved Canny operator to detect the crack edge of the pavement, and the experimental results show the detection effect is more excellent. In the threshold segmentation stage, the invention considers the applicability of the complex condition of pavement, selects the one-dimensional maximum entropy method to segment the image, and makes a comparative experiment. Then it focuses on how to remove the cracked orphans that have been segmented. The invention adopts mathematical morphology to propose the pseudo-cracks of the isolated points, and has achieved good results. Finally, the invention describes a method for determining cracks, and statistically determines the size of the crack to meet the requirements of PCI statistics.

Figure 4:
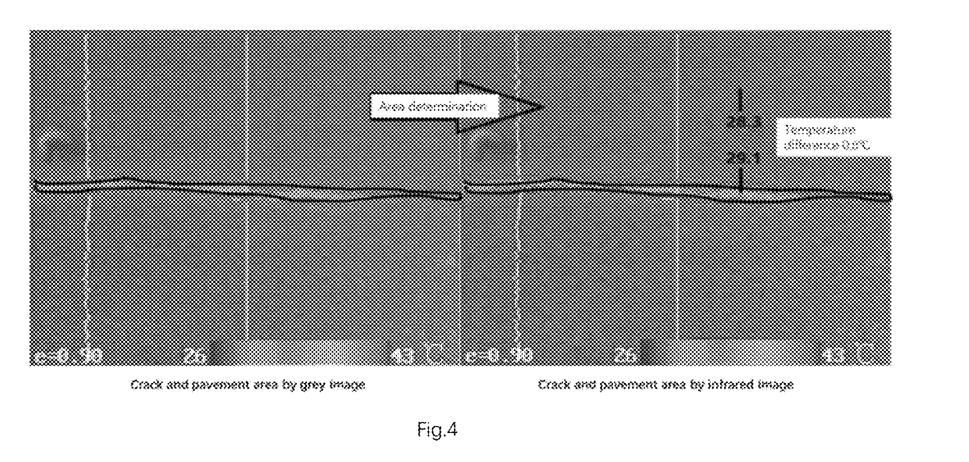
FIG. 4 is schematic diagram of temperature difference in infrared thermal image.

Infrared image processing: Infrared image processing is divided into two major steps. First, grayscale is performed to obtain a grayscale image of the infrared image, Then the crack area and the pavement area (except the crack in the image) can be obtained according to the steps of the ordinary image processing. Then the RGB average values of the two regions are calculated separately, and matched with the legend to obtain the temperature values of the two areas, thereby calculating the temperature difference data between the crack and pavement, as shown in FIG. 4 below.

Figure 5:
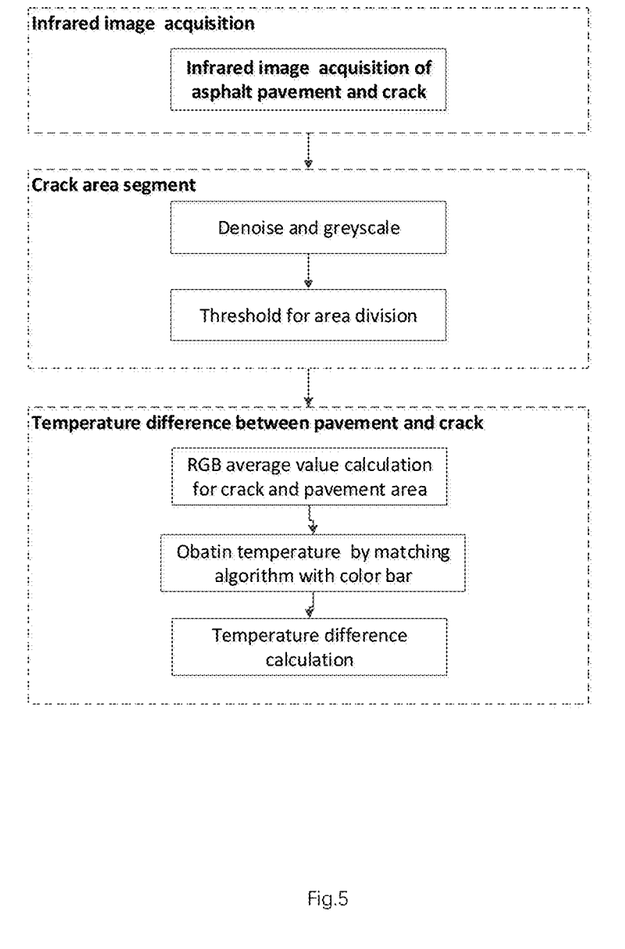
FIG. 5 is a roadmap of image processing technology.
Figure 6:
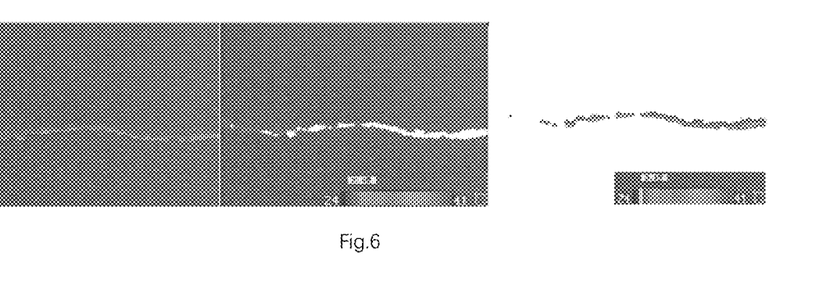
FIG. 6 is the image processing diagram.

After acquisition of the infrared image, we need to process the image to obtain the temperature of the crack and the pavement for further analysis. The crack area and the pavement area can be recognized from the gray-scale information by using the existing mature algorithm, and then the RGB average value of the image in each region is obtained. Finally, the average RGB value is matched with the colorbar sequentially from left to right. Step by taking two pixel widths to ensure the accuracy of the temperature value, calculate the temperature value according to the matched position and color range. The technology roadmap of infrared image processing technology and temperature difference acquisition is shown in FIG. 5. FIG. 6 is a schematic diagram of the image processing.

The unprocessed image contains noise information due to various factors. If these noises are not removed, it will be difficult for subsequent image processing and analysis. Therefore, image preprocessing is very necessary. Preprocessing can remove some redundant information in the image and highlight the target we are interested in, so as to reduce the amount of image information and improve the image quality. First, the image needs to be denoised.

The unprocessed image contains noise information due to various factors. If these noises are not removed, it will be difficult for subsequent image processing and analysis. Therefore, image preprocessing is very necessary. Preprocessing can remove some redundant information in the image and highlight the target we are interested in, so as to reduce the amount of image information and improve the image quality. First, the image needs to be denoised.

Compared with the background, the crack to be identified in the image contains less information. Moreover, in the process of image acquisition and transmission, the resolution and contrast of the image are reduced due to many interference factors. Therefore, the image enhancement after filtering and are taken to make the crack more prominent, providing a basis for the subsequent segmentation recognition algorithm.

Image segmentation means classifying pixels in an image into specific regions with unique properties and extracting the target of interest of specific properties. The purpose of this step of the present invention is to find a crack area and a non-crack area of pavement.

Temperature Difference

After the segmentation of the crack area and non-crack area is completed, the average RGB value of each area can be matched with the colorbar to obtain the temperature.

Figure 7:
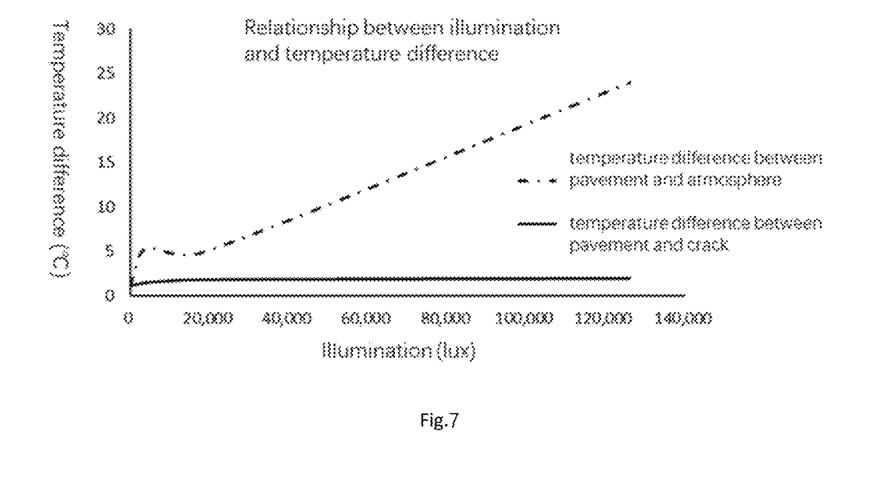
FIG. 7 shows the relationship between illumination and temperature difference.

As shown in FIG. 7, the temperature difference is plotted on the ordinate and the light intensity is plotted on the abscissa. When the light intensity increases, the temperature of pavement will increase as a whole, and the temperature difference between the pavement and the atmospheric will increase. In the actual experiment, when the temperature is 35° C., the asphalt pavement temperature can reach 55° C. when the light intensity is 150,000 Lux. However, the effect of illuminance on the asphalt pavement and the its temperature is almost synchronous, and therefore, the illuminance has substantially no effect on the temperature difference between the crack and pavement.

Therefore, in the case that the pavement is fully tidy and dry, effect factors of the temperature difference are selected as illuminance and atmospheric temperature by querying relevant data. Then through experiments it is confirmed that the illuminance has no effect on the temperature difference between the crack and the pavement. It should be noted that in the experiment, the pavement after rain is selected and the crack temperature is lower than that of the pavement (as completely opposed to the dry condition). The temperature difference will also change greatly as the pavement dries, leading to more complicated result. The present invention selects a completely dry condition for the experiment to avoid the effects of crack moisture.

Finally, it is necessary to determine the influence of atmospheric temperature on the temperature difference between crack and pavement. As mentioned above, the illuminance has almost no effect on the temperature difference between crack and pavement. So the temperature difference at all different temperatures are plotted without considering the illuminance as shown in FIG. 7. The temperature difference of cracks with different degree of growth is different from the sensitivity of atmospheric temperature. The more serious the degree of crack growth, the greater the influence of atmospheric temperature. The overall trend of the temperature difference between crack and pavement increases with the increase of atmospheric temperature.

In summary, the present invention only considers the relationship between the temperature difference between crack and pavement and the atmospheric temperature. At the same time, it can be seen from the above figure that for different degrees of crack growth, the temperature difference is different at different temperatures, so we can reflect the crack growth by detecting the temperature difference between crack and pavement.

Figure 10:
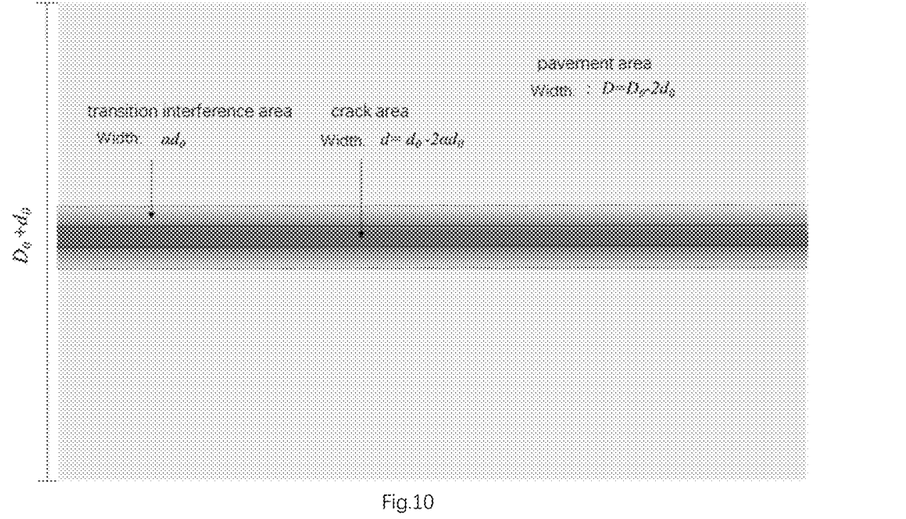
FIG. 10 depicts the asphalt pavement crack area, pavement area and transition interference area.
Figure 11:
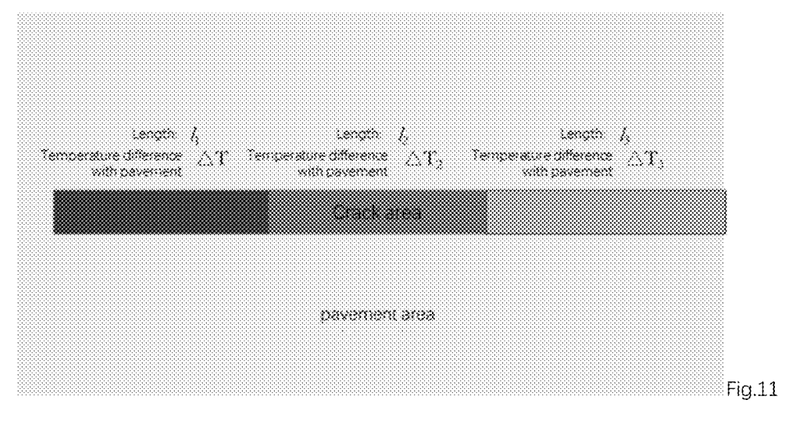
FIG. 11 is a schematic diagram of temperature differences obtained from different crack sections.

About Image Segmentation:

The traditional crack analysis technology based on image analysis only pays attention to the crack itself, like the presence or absence, location and geometry. The transition between the crack and the pavement is basically not considered. The invention mainly needs to obtain the temperature difference of crack and pavement that is necessary to pay attention to. Therefore, the influence of the transition area is supposed to be considered. After the image segmentation, the transition area is cut off because the change of temperature from pavement to the crack is gradual. The temperature of the transition zone between crack and pavement is between the crack center temperature and the pavement temperature. The transition area is the interference area for the temperature acquisition, as shown in FIG. 10. The following measures can be taken to exclude the interference area The transition interference area is small relative to the pavement. Therefore, when the exclusion is performed, a fixed width of area can be cut, which set to w (0.5 cm<w<2.5 cm). Another method is based on the maximum width ratio of the crack, that is, after detecting the crack, the width of crack area is doubled at both upper and lower side, and the remaining region is defined as the pavement area without interference area. Assuming the width of the segmented pavement is $D_0$ and the final width is D determined by the following formula (6). This method can better eliminate the influence of the transition interference area.

$$D = D_0 - 2d_0 \qquad (6)$$

For the crack area, because the width is small, the exclusion of the transition interference area needs to be more accurate. It can be excluded by the method based on the width ratio of the crack area. The crack area of the image segmentation needs to be slimmed down. Assuming the width of the crack is $d_1$, the width of the segmented crack area is $d_0$, the following conditions are satisfied as shown in equation (7):

$$d_1 = d_0 - 2\alpha d_0 \qquad (7)$$

Where $\alpha$ is the ratio of elimination width at both the upper and lower side of the crack width.

After the range of the transition interference area is determined, deleting specifically refers to the following steps. For the pavement area, it is equivalent to moving the image segmentation boundary $d_0$ along the segment boundary to the pavement area to obtain a new boundary. For the crack area, the image segmentation boundary is moved $\alpha d_0$ along the segmentation boundary radially toward the crack area to obtain a new boundary.

About the Calculation of the Zone Temperature:

Asphalt pavement refers to various pavements paved with asphalt materials mixed with mineral materials. Asphalt binder improves the capability of paving granules to resist against damage from traffic loads and natural factors, making the pavement smooth, dust-free, impervious, and durable. The road structure is a band structure in nature, suffering from the damage mainly caused by environmental factors and traffic loads. The physical characteristics of the pavement area are relatively consistent. Therefore, in the infrared image, the temperature value of the pavement area is basically the same, so it is convenient to handle, and it is not necessary to separately consider. Therefore, after image segmentation, the average RGB of the infrared image is calculated.

However, the crack area is usually of a slender shape, such as a two-meter-long crack with width of only a few millimeters. In this case, the severity of the same crack may vary greatly. Only a half-meter-long area of the two-meter-long crack is severe. The average RGB is calculated with a result that this crack needs to be repaired. For another three-meter-long crack, also a half-meter-long area is severe and the average RGB value is calculated showing that the crack growth degree obtained by the temperature difference will be lower than the previous two-meter-long one, and even shows that it does not need to be repaired. Such result is obviously unscientific. Therefore, area division is necessary when we calculate the RGB and a higher weight should be given to the more severe crack area. Then the calculated temperature difference between crack and pavement will be an array, as shown in FIG. 10, different sections of the crack can get different temperature difference.

For the transverse crack, the effective crack area is divided into the p segments by the straight line along the y-axis direction, and each segment length is arbitrary; for the longitudinal crack, the effective crack region is divided into the p segments by the image along the x-axis straight line, and each segment length is arbitrarily; for other types of cracks, no segmentation or angular division into the p segments according to the geometric center of the crack, each segment corresponding to the center angle is arbitrary.

According to the accuracy requirement, the crack area can be divided into $n(n \geq 2)$ segments for consideration. Each segment can be processed according to the technical route described above, that is, grayscale, denoising and image enhancement are performed. After image segmentation, the crack area is obtained and then divided into n segments for subsequent processing, including calculating the average RGB for each segment, and then matching the average RGB with the color value in the legend to determine the temperature of the segment. Then the length of crack in n segments and the temperature difference between crack and pavement $\Delta T$ is calculated, as shown in equation (8) and (9):

$$l=(l_1\ l_2\ \ldots\ l_n) \quad (8)$$

$$\Delta T=(\Delta T_1\ \Delta T_2\ \ldots\ \Delta T_n) \quad (9)$$

Where $l_i$ is the length of crack in the i segment, $\Delta T_i$ the temperature difference between crack and pavement in the i segment.

Then, a weighted average calculation can be performed according to the following formula (10) to obtain a final measured temperature $\Delta T$ difference between the effective pavement area and the effective crack area.

$$\Delta T = \frac{T_1 l_1 + \cdots + T_p l_p}{l_1 + \cdots + l_p} \quad (10)$$

Finally, $\Delta T$ is compared with the reference temperature difference to obtain the relative parameters of crack growth degree. The crack growth index of each segment of is calculated as follows in formula (11):

$$m=(m_1\ m_2\ \ldots\ m_n) \quad (11)$$

Where $m_i$ is the crack growth index of the i segment.

According to the crack growth degree, weights of different sections are given, so the final crack growth index can be obtained as follows in formula (12):

$$m' = \frac{m_1 l_1 + m_2 l_2 + \cdots + m_n l_n}{l_1 + l_2 + \cdots + l_n} \quad (12)$$

The calculation results are rounded off to take 1, 2 or 3, which is the three levels of crack growth.

In the invention, an average distribution method can be adopted, that is $l_1=l_2=\ldots=l_n$. Then, the formula can be converted into the following form (13):

$$m' = \frac{m_1 + m_2 + \cdots + m_n}{n} \quad (13)$$

Crack Growth Index Calculation

The degree of crack growth is divided into three levels of 1, 2 and 3 according to the invention by machine learning in modeling. SVM, as a classification method, maps the linear inseparable samples in low-dimensional space to linear separable samples in multi-dimensional space by the kernel function to obtain a linear classifier. There are many common kernel functions, such as linear kernel functions, polynomial kernel functions, radial basis kernel functions, Sigmoid kernel functions, and composite kernel functions. In the invention, the linear kernel function is first used to classify the 1 and 2 grades to obtain the classification function $l_{12}$, and then classify the 2 and 3 grades to obtain the classification function $l_{23}$. Error exists in the machine learning classification. Therefore, some cracks of less-developed growth are assigned to the category of more serious cracks, vice versa. However, the crack growth index with weights given may contain fractional parts. Although fractional parts do not necessarily make the crack growth index more precise, but it can reflect the relative size. The crack growth index of 2.6 is rounded up to 3 while 2.4 is rounded up to 2 according to previous classification methods. However, 2.6 and 2.4 is actually closed, which is important for the decision-makers. Therefore, in the calculation of the fracture development degree index, the invention can take a decimal point to indicate the calculated relative relationship. It should be noted that 2.4 is not necessarily more serious than 2. As said before, there is the classification error itself. The integer part 2 may be inaccurate. In order to avoid such problems, the invention determines an error term according to the variance of the weighted average calculation method in the calculation, that is, the crack growth index can take one decimal place and is expressed as $m \pm \sigma$.

SVM is adopted here to obtain two classification functions and three level 1 2 3, the more the serious, with the atmospheric temperature as the abscissa and the temperature difference between the crack and the pavement as the ordinate.

The classification function of level 3 and 2:
$$\Delta T_{23}=a_{23}T+b_{23} \quad (14)$$

Where T (° C.) is the atmospheric temperature, $\Delta T$ (° C.) is the temperature difference of crack and pavement; $a_{23}$ is the linear classification function coefficient, ranging from 0.02 to 0.03, and $b_{23}$ is the constant term, ranging from 0.60 to 0.85.

The classification function of level 2 and 1:
$$\Delta T_2=a_{12}T+b_{12} \quad (15)$$

Where T (° C.) is the atmospheric temperature, $\Delta T$ (° C.) is the temperature difference of crack and pavement; $a_{12}$ is the linear classification function coefficient, ranging from 0.0075 to 0.0100, and $b_{12}$ is the constant term, ranging from 0.4 to 0.65.

The test results are judged according to the following steps:

First, calculate $\Delta T_{12}$ and $\Delta T_{23}$ according to the atmospheric temperature and compare $\Delta T$ with $\Delta T_{12}$ and $\Delta T_{23}$. If $\Delta T \leq \Delta T_{12}$, crack growth degree is 1; If $\Delta T_{12} \leq \Delta T \leq \Delta T_{23}$, crack growth degree is 2; If $\Delta T \geq \Delta T_{23}$, crack growth degree is 3.

If the crack area is divided into sections and different weights are given according to the crack growth index, one decimal place is taken here.

The value of the error term σ can be obtained by the following formula (16):

$$\sigma = \sqrt{\frac{\sum_{i=1}^{n}(m_i - \overline{m})^2}{n-1}} \quad (16)$$

$m_i$ is the test result of the i time and the standard deviation is obtained. The crack growth index can be written to one decimal place, and the error is defined by a fixed error term. The error term is obtained from experiments, and the new crack growth index is written as follows (17):

$$m = m \pm a\sigma \quad (17)$$

Where a is the error term coefficient, ranging from 1 to 3.

Image Acquisition

Image acquisition can directly perform two-way video capture, and then the real-time image processing is performed to obtain pavement disease information as well as spatial and temporal coordinates.

The above image acquisition methods have higher performance requirements for the processing terminal, and the image processing algorithm is more complicated, but the requirements for the device are less. Besides, accurate measurement in the speed of the mobile platform is not necessary. Another image acquisition method needs to be coordinated by the photoelectric encoder and the synchronous controller. The photoelectric encoder accurately acquires the speed of the mobile platform. The synchronous controller determines the image shooting at a certain distance from the platform speed, and further triggers the two cameras simultaneously. Image acquisition is performed, and then the image data is transmitted to the processing terminal. The processing terminal directly processes each image to obtain disease data and store the image. This method can reduce the requirements of the algorithm and the processing terminal, that is, reduce the complexity of the algorithm by adding hardware.

Photoelectric encoder: Photoelectric encoder is a kind of sensor that converts the mechanical geometric displacement on the output shaft into pulse or digital quantity by photoelectric conversion. It is the most widely used sensor. A general photoelectric encoder is mainly composed of a grating disk and a photoelectric detecting device. In the servo system, since the photoelectric code disk is coaxial with the motor, when the motor rotates, the grating disk rotates at the same speed as the motor. Detection device composed of an electronic component such as a light emitting diode detects and outputs a plurality of pulse signals. The current motor speed can be reflected by calculating the number of photoelectric encoder output pulses per second. In addition, in order to determine the direction of rotation, the code wheel can also provide two channels of optical code output with a phase difference of 90°, and determine the steering of the motor according to the state change of the two-channel optical code. According to the detection principle, the encoder can be divided into optical encoder, magnetic encoder, inductive encoder and capacitive encoder. According to its scale method and signal output form, it can be divided into three types: incremental encoder, absolute encoder and hybrid encoder.

Synchronous controller: Synchronous controller coordinates the position, speed and torque between the master and the slave according to a certain ratio. There are two types of synchronous controllers. One type is used in the same way as the tension system. The tension controller is also a synchronous control device. This type of synchronization is realized by the synchronization of the same speed and torque. The other type is the space positioning controller, like position synchronization. It is a kind of position tracking between axes, which is generally used in the linkage between the axes of robots, CNC machine tools, flying shears, etc. At present, two types of the synchronous controller are in the market: class with embedded setting parameters and direct programmable class. With the development of technology, the application of programmable class slowly surpasses the former, which can be connected and operated by field bus or other communication technology and other devices.

Test Environment

The temperature information of pavement and crack is used to detect the crack growth degree. However, the temperature of pavement changes greatly and is influenced by many environmental factors. The requirements for the test environment are higher than the crack recognition based on ordinary images. We determine the environmental requirements according to the law in the change of the temperature, which ensures the reliability of the final model.

During the day, the maximum temperature of the pavement appears almost simultaneously with the daily maximum temperature. During the daily sunrise and sunset, the temperature at each depth of the road is always approximately equal. The lowest temperature of the road surface also appears almost simultaneously with the daily minimum temperature. As the depth increases, the time at which the daily minimum temperature occurs at different depths gradually becomes later. That is, although the solar radiation has a similar law to the temperature of the pavement, the influence on the pavement temperature is hysteretic and cumulative. Features. The test environment is shown in FIG. 2 and can be summarized as follows:

(1) Sunny day. Temperature of the pavement is variable and is easy to be disturbed by climatic conditions. Therefore, environmental factors should be stable and single. Sunny daytime is selected for experiment. The temperature difference between the crack and the pavement temperature at night is small, as shown in the figure, which is considered to be related to the regular temperature variation of the asphalt.

(2) Effective time for data collection is from 8 am to 4 pm. From the above analysis, during sunset and sunrise, the temperature at each depth inside the pavement is always approximately equal. Therefore, the temperature difference between the pavement and the crack is small during this period, and it has been verified by experiments.

(3) The pavement is completely dry. After the rain, the pavement and cracks are all infiltrated by water, and the temperature is basically the same. The detection result of wet pavement will be unstable due to evaporation of water. When the pavement is dry and the crack is wet, and the water will affect the temperature of the crack. In the situation, temperature of the crack is lower than pavement.

(4) The pavement is clean. In order to ensure that the infrared rays of cracks and pavement can be detected by the thermal imager, it is necessary to ensure that the pavement is clean with elimination of the effect caused by soil, impurities and oil stains.

IMPLEMENTATION (1) Model Formulation

Considering the differences in climatic conditions in different regions, the relationship between the temperature difference of crack and pavement and the growth degree works in certain region. First, a certain number of infrared image acquisition of cracks in a suitable collection environment is performed. Then, SVM is carried out according to the atmospheric temperature, the temperature difference between the pavement and the crack and the crack growth degree to obtain the classification function. Then the detection model in a certain season in this region is formulated.

(2) Environment Determination

The predictive relationship model works under certain environmental conditions to ensure accuracy. The test environment can be summarized as follows:

a) Sunny day
b) Effective time for data collection is from 8 am to 4 pm.
c) The pavement is completely dry.
d) The pavement is clean.

(3) Data Acquisition

Figure 12:
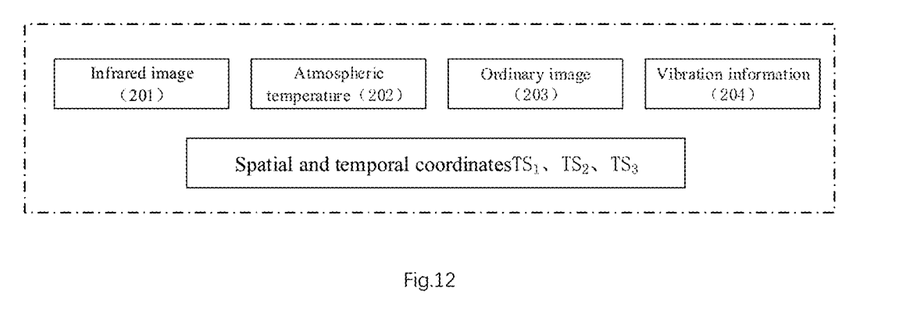
FIG. 12 depicts the application phase samples data, including infrared image (201), atmospheric temperature (202), ordinary image (203), vibration information (204), spatial and temporal coordinates $TS_1$, $TS_2$, and $TS_3$.

The ordinary camera (with night vision function) and the infrared camera (thermal measurement) are fixed on the mobile platform. The pavement inspection is carried out in the determined environment. First, a specific lane is selected to record the initial lane information, and the inspection speed can reach up to 80 km/h, two cameras are used for real-time image acquisition during the inspection. The frequency is greater than or equal to 60 Hz. The vibration sensor acquisition frequency is at least 100 Hz. The real-time high-frequency sampling is performed. At the same time, the positioning device and system time are used for real-time spatial and temporal coordinate acquisition. The application scenario is asphalt pavement for various grades of road. Here is the application phase, and the specific sampling data is shown in FIG. 12.

(4) Data Processing

Firstly, real-time processing of two images is carried out. Each image is treated with a road disease identification algorithm, and the images are classified and stored in diseased manner and disease-free manner. Image in diseased manner is further identified for disease type. Image with crack is further identified for the growth degree based on the infrared image. Images with crack are collected to form the log information, that is matched with the position information. The same crack may exist in multiple images. After processing, each image will receive disease information. After matching with the position information, the disease can be determined. The uniqueness is that there is only one disease type at the same position. Finally, the disease information is uploaded to the central server for display and application.

At the same time, the vibration signal is processed, and the roughness information of the road segment is calculated in real time through the high-frequency vibration signal, and matched with the spatial and temporal coordinates to form a complete roughness detection information, which is then uploaded to the server database for display and application.

(5) Data Release

Data release is divided into two levels. The first layer is the display of the working layer. The data release layer is configured on the vehicle side. The display terminal is directly connected to the processing terminal. The data is derived from the real-time processing terminal, mainly to visualize the data stream and the working status without any interactive interface. The working conditions are divided into normal, abnormal and error. The display of the data flow assists the relevant personnel to eliminate the abnormal working conditions. The wrong working condition is a device problem and needs to be checked for downtime. The abnormal working conditions are mainly the abnormal collection conditions such as unsatisfied climatic conditions or too fast moving of platform.

The second layer is the release of the application layer, mainly to visualize Web form, which is divided into log interface and map visualization interface. The log page can realize the operation of querying, exporting and importing data. The visualization interface displays the position and information of the disease on the two-dimensional map, which can be switched to the roughness display mode at the same time.

The invention claimed is:

1. A system for detecting crack growth degree of an asphalt pavement based on binocular image analysis, the system comprising:
  a thermometric infrared camera for capturing infrared images of the asphalt pavement that comprise information of an atmospheric temperature;
  an active infrared image sensor for capturing ordinary images of the asphalt pavement;
  a vehicle positioning device for determining spatial and temporal coordinate $TS_1$, $TS_2$, $TS_3$;
  a three-axis acceleration sensor for collecting vibration information of a rear axle of a vehicle;
  a mobile platform onto which the thermometric infrared camera, the active infrared image sensor, the vehicle positioning device and the three-axis acceleration sensor are fixed, the mobile platform being provided on the vehicle to continuously move with the vehicle; and
  one or more processors configured to perform:
    a) collecting at least ten sample infrared images of cracks on the asphalt pavement, recording a sample atmospheric temperature and a crack growth degree; ranking the crack growth degree into three levels of 1, 2 and 3 according to a traditional crack severity classification method;
    b) processing the sample infrared images in step a), cutting off transition zone between said crack samples and said asphalt pavement and obtaining measured temperature difference data between said crack samples and said asphalt pavement in said sample infrared images;
c) based on the measured temperature difference data in step b), the atmospheric temperature and said crack growth degree in step a), obtaining two classification functions by Support Vector Machine: $\Delta T_{12}=a_{12}T+b_{12}$ and $\Delta T_{23}=a_{23}T+b_{23}$, where T (° C.) is an independent variable, representing the atmospheric temperature, $\Delta T_{12}$ and $\Delta T_{23}$ are dependent variables, representing the reference temperature difference data;
h) matching the infrared images, the atmospheric temperature and the ordinary images with spatial and temporal coordinate $TS_1$ and $TS_2$ to obtain disease information;
i) processing the vibration information of the rear axle of the vehicle and matching said vibration information of the rear axle with the spatial and temporal coordinate $TS_3$ to obtain roughness information;
j) uploading the disease information and the roughness information to a server database; and
k) displaying the disease information and the roughness information of the server database, and identifying and locating crack areas on the asphalt pavement based on the disease information and the roughness information.

2. The system according to claim 1, wherein step h) includes the following sub-steps:
$h_1$) processing ordinary images by algorithm for pavement disease identification model to obtain the presence and type of the disease;
$h_2$) processing infrared images by algorithm for pavement disease identification model to obtain crack area;
$h_3$) processing infrared images by algorithm for pavement disease identification model to obtain crack growth degree;
$h_4$) labeling spatial and temporal coordinate $TS_1$ and $TS_2$ with the presence and type of the disease, crack area and crack growth degree.

3. The system according to claim 2, wherein step i) includes the following sub-steps:
$i_1$) processing vibration information by the roughness detection algorithm based on power spectral density to obtain the roughness information of the whole road section;
$i_2$) labeling spatial and temporal coordinate $TS_3$ with the roughness information said in $i_1$, where time coordinates are up to minutes and space coordinates to meters.

4. The system according to claim 1, wherein sub-step $h_3$) includes:
$h_{31}$) matching the infrared images of the pavement with the legend to obtain the measured temperature values of the pavement $T_0$;
$h_{32}$) dividing the crack area into p (p≥2) segments of the length $l_1 \ldots l_p$ and matching each segment with legend to obtain the measured temperature $T_1 \ldots T_p$;
$h_{33}$) subtracting $T_0$ from the measured temperature $T_1 \ldots T_p$ to obtain the measured temperature difference of each segment $\Delta T_1 \ldots \Delta T_p$;
$h_{34}$) calculating the weighted mean according to the following formula to obtain a final measured temperature difference $\Delta T$;

$$\Delta T = \frac{T_1 l_1 + \cdots + T_p l_p}{l_1 + \cdots + l_p}$$

$h_{35}$) introducing atmospheric temperature into the classification function $\Delta T_{12}=a_{12}T+b_{12}$ to obtain the reference temperature difference $\Delta T_{12}$;
$h_{36}$) introducing atmospheric temperature into the classification function $\Delta T_{23}=a_{23}T+b_{23}$ to obtain the reference temperature difference $\Delta T_{23}$;
$h_{37}$) comparing $\Delta T$ with $\Delta T_{12}$ and $\Delta T_{23}$; if $\Delta T \leq \Delta T_{12}$, crack growth degree is 1; if $\Delta T_{12} \leq \Delta T \leq \Delta T_{23}$, crack growth degree is 2; and if $\Delta T \geq \Delta T_{23}$, crack growth degree is 3.

5. The system according to claim 4, wherein step i) includes the following sub-steps:
$i_1$) processing vibration information by the roughness detection algorithm based on power spectral density to obtain the roughness information of the whole road section;
$i_2$) labeling spatial and temporal coordinate $TS_3$ with the roughness information said in $i_1$, where time coordinates are up to minutes and space coordinates to meters.

6. The system according to claim 1, wherein step i) includes the following sub-steps:
$i_1$) processing vibration information by the roughness detection algorithm based on power spectral density to obtain the roughness information of the whole road section;
$i_2$) labeling spatial and temporal coordinate $TS_3$ with the roughness information said in ii, where time coordinates are up to minutes and space coordinates to meters.

7. The system according to claim 1, wherein step i) includes the following sub-steps:
$i_1$) processing vibration information by the roughness detection algorithm based on power spectral density to obtain the roughness information of the whole road section;
$i_2$) labeling spatial and temporal coordinate $TS_3$ with the roughness information said in ii, where time coordinates are up to minutes and space coordinates to meters.

8. The system according to claim 1, wherein step i) includes the following sub-steps:
$i_1$) processing vibration information by the roughness detection algorithm based on power spectral density to obtain the roughness information of the whole road section;
$i_2$) labeling spatial and temporal coordinate $TS_3$ with the roughness information said in $i_1$, where time coordinates are up to minutes and space coordinates to meters.

9. The system according to claim 1, wherein step i) includes the following sub-steps:
$i_1$) processing vibration information by the roughness detection algorithm based on power spectral density to obtain the roughness information of the whole road section;
$i_2$) labeling spatial and temporal coordinate $TS_3$ with the roughness information said in $i_1$, where time coordinates are up to minutes and space coordinates to meters.

10. The system according to claim 1, wherein step i) includes the following sub-steps:
$i_1$) processing vibration information by the roughness detection algorithm based on power spectral density to obtain the roughness information of the whole road section;
$i_2$) labeling spatial and temporal coordinate $TS_3$ with the roughness information said in $i_1$, where time coordinates are up to minutes and space coordinates to meters.

11. The system according to claim 1, wherein step k) includes the following sub-steps:

$k_1$) displaying the disease information and roughness information stored in the server database a in the visual interface through the form of category and time series log;

$k_2$) map visualizing the disease information and roughness information stored in the server database by category and spatial sequence.

12. The system according to claim 11, wherein: in sub-step $k_1$):

the said log form can realize classified querying and sorting by time and space;

the said log form can import external disease information and realize saving and calling;

the said log supports report generation, statistical chart visualization and analysis model access;

in sub-step $k_2$):

the said map visualization can be classified, viewed and sorted by space;

the said map visualization supports single point and single disease query and generates report forms.

13. The system according to claim 1, wherein step k) includes the following sub-steps:

$k_1$) displaying the disease information and roughness information stored in the server database a in the visual interface through the form of category and time series log;

$k_2$) map visualizing the disease information and roughness information stored in the server database by category and spatial sequence.

14. The system according to claim 1, wherein step k) includes the following sub-steps:

$k_1$) displaying the disease information and roughness information stored in the server database a in the visual interface through the form of category and time series log;

$k_2$) map visualizing the disease information and roughness information stored in the server database by category and spatial sequence.

15. The system according to claim 1, wherein step k) includes the following sub-steps:

$k_1$) displaying the disease information and roughness information stored in the server database a in the visual interface through the form of category and time series log;

$k_2$) map visualizing the disease information and roughness information stored in the server database by category and spatial sequence.

16. The system according to claim 1, wherein step k) includes the following sub-steps:

$k_1$) displaying the disease information and roughness information stored in the server database a in the visual interface through the form of category and time series log;

$k_2$) map visualizing the disease information and roughness information stored in the server database by category and spatial sequence.

* * * * *